United States Patent [19]

Stankowski et al.

[11] Patent Number: 5,439,587
[45] Date of Patent: Aug. 8, 1995

[54] SELF PRIMING FILTER APPARATUS

[75] Inventors: Ralph J. Stankowski, Westford; Michael C. Heath, Chelmsford; Douglas A. Boucher, Billerica, all of Mass.

[73] Assignee: Millipore Corporation, Bedford, Mass.

[21] Appl. No.: 98,171

[22] Filed: Jul. 27, 1993

[51] Int. Cl.⁶ .................... A61M 5/165; B01D 19/00
[52] U.S. Cl. ................ 210/321.64; 210/321.75; 210/321.84; 210/436; 210/455; 210/472; 210/346; 210/446; 96/6; 96/219; 604/126; 604/406; 422/101
[58] Field of Search ............... 96/6, 155, 219; 95/46, 95/260; 210/436, 455, 472, 321.64, 321.75, 321.84, 446, 346, 347; 422/101; 604/126, 406

[56] References Cited

U.S. PATENT DOCUMENTS

| | | |
|---|---|---|
| 3,523,408 | 8/1970 | Rosenberg . |
| 3,631,654 | 1/1972 | Riely . |
| 3,650,093 | 3/1972 | Rosenberg . |
| 3,730,353 | 5/1973 | Trasen . |
| 3,803,810 | 4/1974 | Rosenberg . |
| 3,854,907 | 12/1974 | Rising . |
| 3,905,905 | 9/1975 | O'Leary . |
| 3,993,062 | 11/1976 | Jess . |
| 4,004,587 | 1/1977 | Jess . |
| 4,009,714 | 3/1977 | Hammer . |
| 4,031,891 | 6/1977 | Jess . |
| 4,116,646 | 9/1978 | Edwards . |
| 4,177,149 | 12/1979 | Rosenberg . |
| 4,190,426 | 2/1980 | Ruschke . |
| 4,227,525 | 10/1980 | Lundquist . |
| 4,276,170 | 6/1981 | Vaillancourt . |
| 4,278,084 | 7/1981 | Pope . |
| 4,294,594 | 10/1981 | Sloane . |
| 4,341,538 | 7/1982 | Vadnay . |
| 4,369,112 | 1/1983 | Vincent . |
| 4,400,277 | 8/1983 | Leason . |
| 4,411,783 | 10/1983 | Dickens . |
| 4,490,254 | 12/1984 | Gordon . |
| 4,500,426 | 2/1985 | Ishii . |
| 4,501,663 | 2/1985 | Merrill . |
| 4,515,606 | 5/1985 | de Winter . |
| 4,525,182 | 6/1985 | Rising . |
| 4,568,366 | 2/1986 | Fredrick . |
| 4,572,724 | 2/1986 | Rosenberg . |
| 4,615,694 | 10/1986 | Raines . |
| 4,690,762 | 9/1987 | Katsura . |
| 4,793,928 | 12/1988 | Tsukamoto . |
| 4,828,587 | 5/1989 | Baurmeister . |
| 4,906,260 | 3/1990 | Emheiser . |
| 4,919,802 | 4/1990 | Katsura . |
| 4,932,987 | 6/1990 | Molina . |
| 4,964,984 | 10/1990 | Reeder . |
| 5,013,339 | 5/1991 | Mahoney . |
| 5,019,140 | 5/1991 | Bowser . |
| 5,037,457 | 8/1991 | Goldsmith . |
| 5,045,096 | 9/1991 | Quang . |
| 5,221,474 | 6/1993 | Yokono . |
| 5,252,222 | 10/1993 | Matkovich . |
| 5,258,127 | 11/1993 | Gsell . |
| 5,290,237 | 3/1994 | Verkaart . |
| 5,348,646 | 9/1994 | Costello . |

FOREIGN PATENT DOCUMENTS 3205229 8/1983 Germany .

*Primary Examiner*—Thomas M. Lithgow
*Attorney, Agent, or Firm*—Andrew T. Karnakis; Paul J. Cook

[57] ABSTRACT

A self-priming filter holder for filtration of intravenous liquids is provided and is formed of one or two housing portions sealed to a core portion. The core portion has one or two ribbed surfaces forming a plurality of flow paths sealed at one end and open at a second end and at least one channel preferably larger than the flow paths. The channel(s) is in fluid communication with the flow paths and an outlet. An inlet is provided to the interior of the housing portion(s) which are sealed from the ribbed surfaces by hydrophilic membranes. The housing portion(s) can be provided with gas vents sealed with hydrophobic membranes. Fluids pass through the flow paths in one direction and through the channel(s) in an opposite direction to remove gas from the flow paths and channels prior to use.

20 Claims, 4 Drawing Sheets

5,439,587

SELF PRIMING FILTER APPARATUS

BACKGROUND OF THE INVENTION

This invention relates to a filter holder useful in the filtration of intravenous fluids as they are supplied to patients undergoing intravenous therapy. More particularly, the invention relates to a holder for a microporous membrane filter adapted to separate gases and liquids while performing the filtration function.

Filter holder designs adapted to separate liquids from gases entrained therein while filtering the liquid are known. Specific designs for such filter holders are shown, for example, in U.S. Pat. Nos. 3,523,408; 3,631,654; 3,854,907 and 4,521,182.

It is necessary to remove air from intravenous fluid before the fluid enters the vein of a patient since bubbles which enter a vein can cause an air embolism with substantial danger of death to the patient. For this reason, filters which perform a liquid-gas separation have found particular application in the in-line filtration of intravenous fluids, i.e., filtration as the fluid is being supplied to the patient.

In general, the liquid containing gases entrained therein is supplied to a chamber having an inlet and an outlet. The outlet is separated from the inlet by a filtration material which is hydrophilic, i.e., wetted by the aqueous liquid. The typical small pore size of the hydrophilic filter prevents gas from passing through the filter at the usual operating pressures. Thus, the gas is retained in the housing while the liquid passes through the filter to the outlet. Often the filter device has a second outlet which is covered by a second filtration material which is hydrophobic, i.e., which is not wetted by the liquid. Pressure within the chamber will tend to force gas which is retained by the hydrophilic filter through the second filtration material which thus acts as a gas vent.

For example, to prepare an in-line intravenous filter for use on a patient, air must be purged from the filter chamber and connected tubing in a priming procedure Of particular importance is the removal of air which is in the tubing and filter device downstream of the hydrophilic filter. Whereas air which remains upstream of the hydrophilic filter will be retained by the filter, any air which remains downstream can pass unimpeded into the blood stream of the patient.

The filtration material typically is supported on an array of small ribs and channels which are formed in the chamber wall. In use, the channels conduct the filtered liquid to the outlet. During priming, the liquid displaces air from within the filtration material and first forms droplets on the downstream surface of the filtration material. A droplet often fills the cross-section of a channel without displacing all the air from that channel. Thus, small air bubbles may remain in the array of channels. The standard procedure for priming the prior art intravenous filtration devices is to fill the device with solution in its in-line (hanging) position, i.e., with its inlet at the top and outlet at the bottom. When the device fills with liquid upstream of the hydrophilic filter, it is inverted to purge from the device any remaining air which is located downstream of the hydrophilic filter. Small gas bubbles trapped in the narrow channels do not dislodge easily, which wastes liquid and time. Sometimes additional manipulation, such as tapping on the housing be required to dislodge the bubbles.

Accordingly, it would be desirable to provide a filter device for liquids such as intravenous fluid which is self priming whereby gas is eliminated rapidly from its interior. In addition, it would be desirable to provide such a device which is made in one piece, does not require additional supporting devices and which has a small hold-up volume.

SUMMARY OF THE INVENTION

In accordance with this invention, a self-priming filter holder is provided which is formed of two housing portions joined about their periphery. An inlet and an outlet fitting are formed integrally with the housing portions. A hydrophobic filter can be sealed to an area of the inner surface of a first housing portion to cover vent holes to the atmosphere in order to permit trapped air upstream of the hydrophilic filter to vent from the filter holder. The inner surface of the second housing portion has a ribbed surface to which is sealed a hydrophilic filter. The ribbed surface defines liquid flow paths which collect liquid flowing through the hydrophilic filter and direct it upwardly toward the inlet and to a collection channel and thence downwardly to the outlet when the device is in a hanging position. In use, liquid passes from the inlet onto and through the surface of the hydrophilic filter to form a liquid filtrate. The liquid filtrate passes upwardly within liquid flow paths which are sealed at one end adjacent the outlet and then downwardly in channels which are, in turn, in fluid communication with the outlet. Air in the flow paths and channels is forced by the liquid to the outlet. It is preferred that the channels which are in fluid communication with the flow paths have a larger cross-sectional area than the flow paths in order to promote fluid flow toward the outlet. Initial liquid flow tends to be greater through the bottom portion of the hydrophilic filter than through the top, aiding the upward displacement of air and reducing the likelihood that small bubbles will be trapped in the flow paths and the need to invert the device. After the air has been removed from the filter device and it and the tubing downstream of the filter holder have been filled with liquid, it is in condition for use.

DESCRIPTION OF SPECIFIC EMBODIMENTS

The filter holder of this invention is based upon the use of a filter support having a plurality of flow paths sealed at the end which direct liquid toward an inlet end of the device and having at least one channel which collects the liquid from the flow paths and directs it downward toward the outlet of the device. Upward flow in the flow paths promotes the flow of air up and out of the flow paths and into the channel or channels. The channel(s) promote the flow of air from the flow paths to the outlet. As used herein, the terms "upward" or "upwardly" refer to the direction toward the inlet when the filter device is in a hanging position while the terms "downward" or "downwardly: refer to the direction toward the outlet. The term "flow path" as used herein refers to depressions in the ribbed surface which are sealed at one end. The term "channels" as used herein refers to depressions in the ribbed surfaces which are open at both ends and which are in fluid communication with the flow paths and outlet.

The channel(s) preferably are larger than the flow paths in order to promote the desired fluid flow.

The hydrophilic filter preferably is sealed to the support surface not only about its periphery but also at the bottom and sides of the flow path to form U-shaped pockets open at the top to ensure that the flow of gas and liquid will be upward in the first channels.

In one embodiment, the filter holder of his invention can be formed from two housing portions and a core portion wherein the core portion has two ribbed surfaces forming flow paths and channels. Hydrophilic membranes cover the ribbed surface as described above so that liquid must pass through the hydrophilic membrane prior to contacting the ribbed surfaces. The use of two ribbed surfaces desirably increases the capacity of the filter holder to filter liquid.

Figure 1:
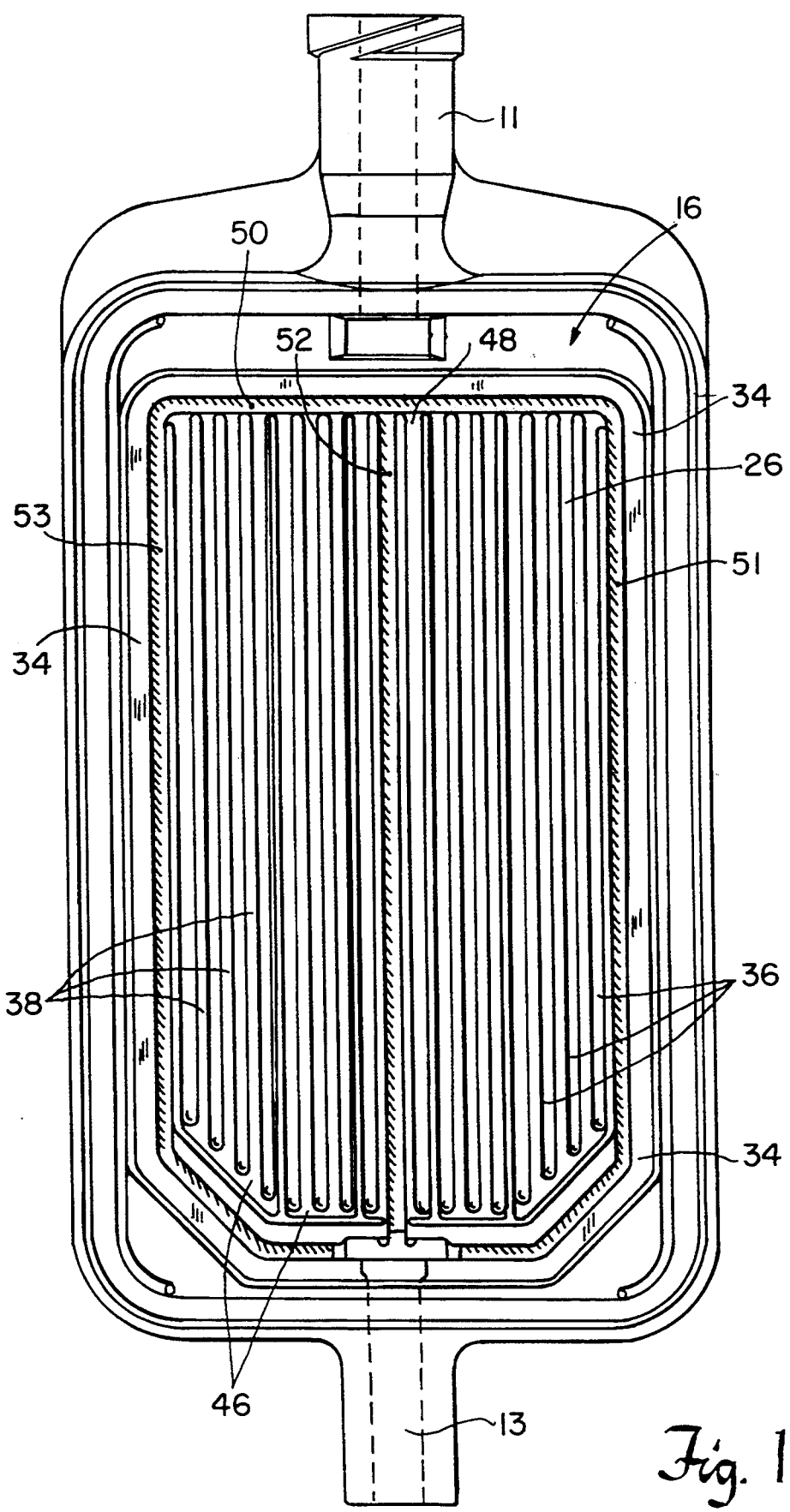
FIG. 1 is a top view of the ribbed surface of the filter support of this invention.
Figure 2:
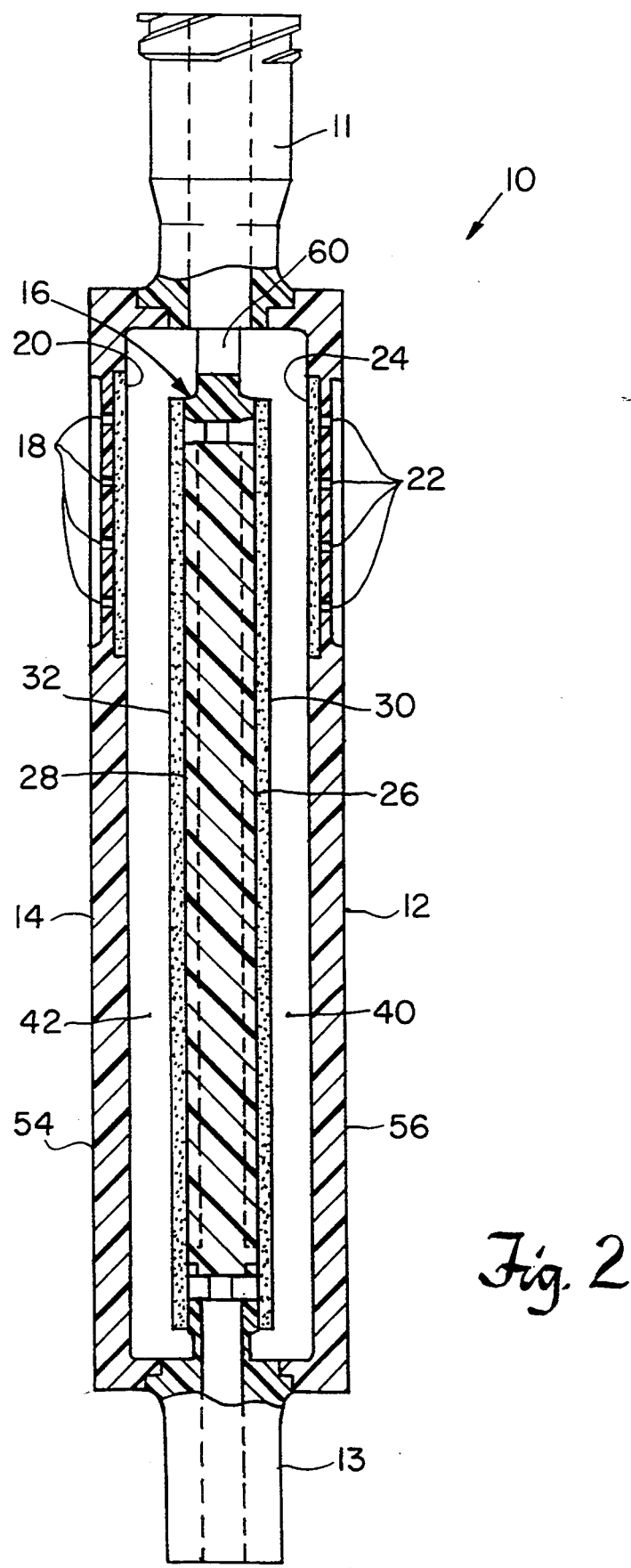
FIG. 2 is a cross sectional view of the assembly of the preferred embodiment of this invention.

Referring to the FIGS. 1 and 2, the vented filter holder 10 includes a first housing portion 12, a second housing portion 14 and a core portion 16. The first housing portion 12 includes vent holes 18 to which are sealed a hydrophobic membrane 20. The second housing portion 14 includes vent holes 22 to which are sealed a hydrophobic membrane 24. The core 16 includes two opposing ribbed surfaces 26 and 28 to which are sealed hydrophilic membranes 30 and 32. The membrane 30 is sealed to an inner peripheral surface 34 so that all of the ribs 36, adjacent flow paths 38 and channels 50, 51, 52 and 53 are sealed by the membrane 30 from the inner volume 40. Similarly, membrane 32 seals the ribs 28 and adjacent flow paths and channels from inner volume 42. The flow paths 38 are sealed at one end 46 and are opened at the opposite end 48 so that flow from the flow paths 38 is directed only into channel 50 adjacent inlet 11 and away from outlet 13. Channel 50 is in fluid communication with outlet 13 channels 50, 51, 52 and 53 preferably are larger than flow paths 38 in order to promote flow from flow paths 38 into these larger channels. It is preferred that the larger channels be deeper than the flow paths 38 in order to attain this larger cross-sectional area and in order to adequately support the filter against liquid pressure and to permit flow paths or channel occlusion. It is to be understood that only one, or a plurality of channels in communication with channel 50 and outlet 13 can be used in order to promote flow from the flow paths 38 to channel 50. The channels and flow paths can be parallel to the direction Of flow through the inlet 11 and the outlet 13 or they can be angled to this direction if desired. In use, with reference to FIGS. 1 and 2, the inlet 11 is connected to a supply of liquid to be filtered, which may be an intravenous fluid. The liquid enters the inlet 11 and partially fills the volumes 40 and 42 by being passed through port 60. Air in volumes 40 and 42 is forced by the liquid toward the top surface of filter holder 10 and vents 18 and is passed through membranes 20 and 24 to the atmosphere. Air in flow paths 38 is forced upwardly toward channel 50 by liquid passing through hydrophilic membranes 30 and 32. The air then is passed from channel 50 to channels 51, 52 and 53 and then to outlet 13 because the flow paths 38 are sealed at surface 46 and open at surface 48. After all of the air has been observed to have been removed from flow paths 38, the filter holder and tubing connected to outlet 13 can be secured intravenously to a patient.

Figure 3:
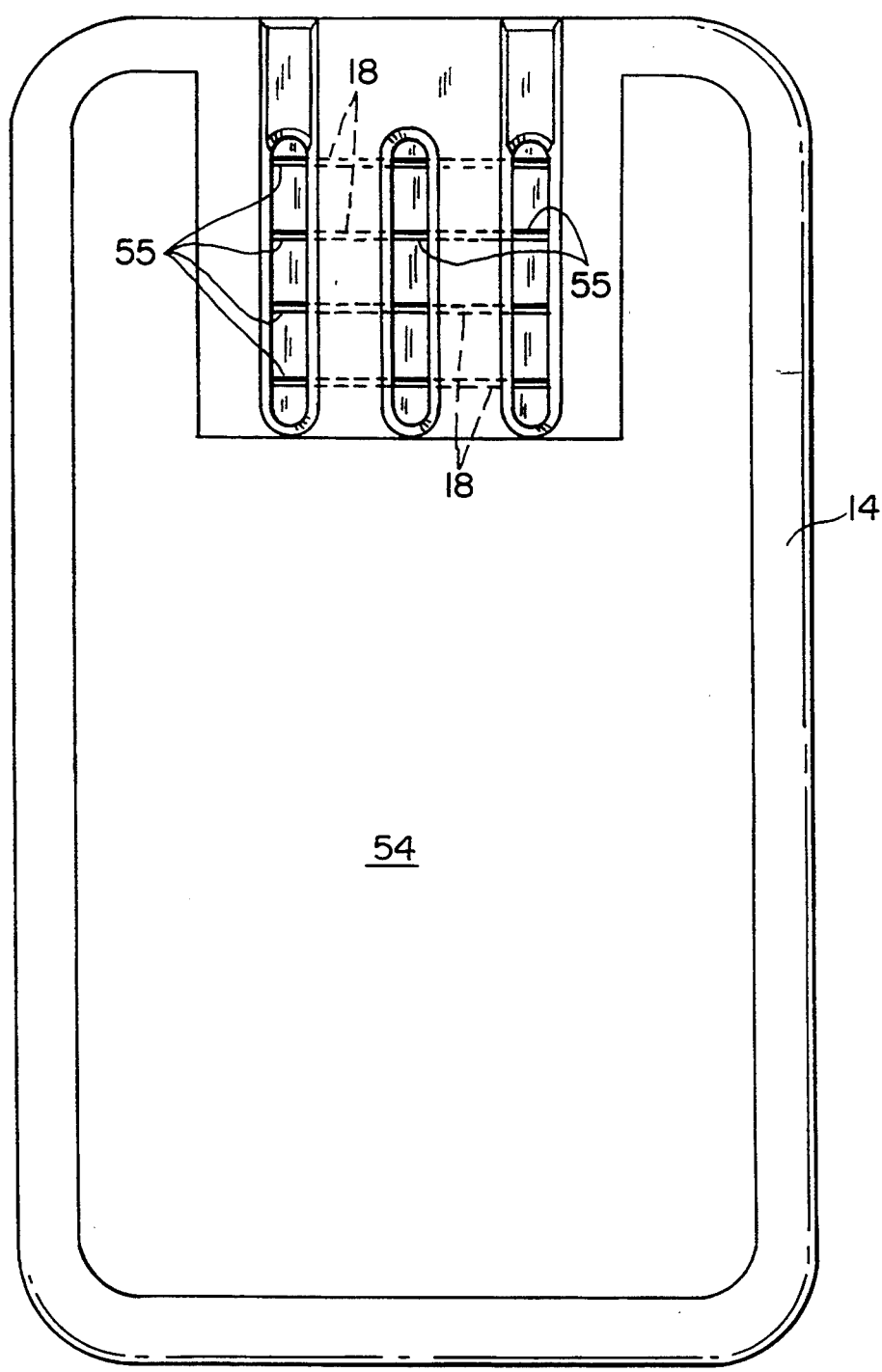
FIG. 3 is a top view of the outside surface of a housing for the filter device of this invention.

Referring to FIG. 3, the outside surface 54 of housing portion 14 is shown wherein portions 55 of vents 18 are open to the atmosphere. The outside surface 56 of housing portion 12 is the same as surface 54 wherein portions of vents 22 are open to the atmosphere. While use of vents and hydrophobic filters is preferred to remove air upstream of the hydrophilic membranes 30 and 32, the vents and hydrophobic filters are not essential since the air cannot pass through the hydrophilic membranes while liquid can be filtered.

Figure 4:
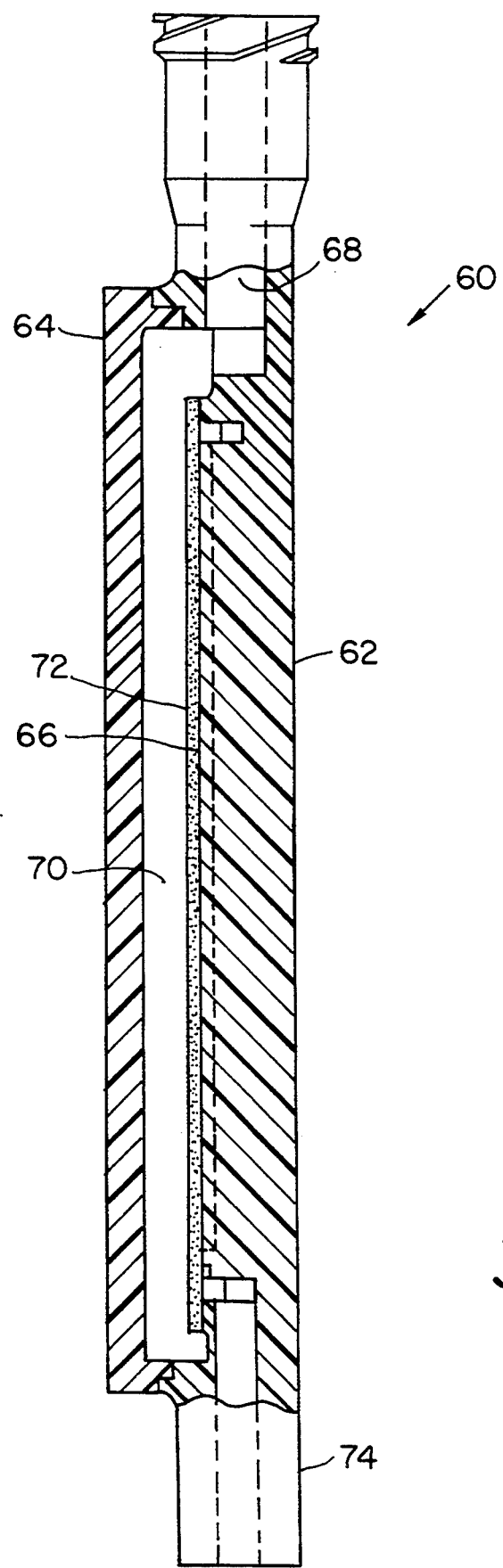
FIG. 4 is a cross-sectional view of the filter holder of this invention having one ribbed surface.

Referring to FIG. 4, an embodiment of this invention is shown having only one ribbed surface and being free of vents and a hydrophobic filter. This filter holder 60 includes a core portion 62 which also serves as a housing portion and which is sealed to a housing portion 64. The ribbed surface 66 can be the same as that shown in FIG. 1. Liquid passes through inlet 68 into volume 70 and through hydrophilic filter 72 to form a filtrate which then flows within ribbed surface 66 in the manner described above with reference to FIG. 1 and thence through outlet 74.

The liquid wettable hydrophilic filter material is preferably a microporous membrane filter made of mixed esters of cellulose. This material is available in a wide range of pore sizes and the particular pore size depends upon the particular use for which the unit is designed. For use in intravenous therapy, it has been found that mean pore sizes in the range 5.0 micrometers to 0.1 micrometers are preferred. Liquid wettable filter material of the foregoing description is available from the Millipore Corporation, Bedford, Mass. as its type MF filter.

The non-wettable hydrophobic filter material may be one of the foregoing materials which has been chemically treated to render it non-wettable. However, it is preferred to use a filter made of polytetrafluoroethylene or polyvinylidene fluoride which is inherently non-wettable. For use in intravenous filter holders made according to this invention, a microporous polytetrafluoroethylene filter having a pore size of 0.2 micrometers has been used. Filters of this material are also available from Millipore Corporation under the trademark Fluoropore as its grade FG.

The filter holder 10 is preferably molded of a polyester resin. This permits both the wettable and non-wettable filters to be heat sealed or solvent sealed directly to the support member in the locations shown. Heat sealing of the filter material can also be accomplished when the support is molded of polyvinylchloride. When the support member is made of a plastic or of metal so that heat sealing is not possible, the filter materials may be bonded to the filter housing portions 12 and 14 with solvents or adhesives as appropriate.

We claim:
1. A filter apparatus comprising
a first housing portion having a first periphery and a second housing portion having a second periphery, said first periphery being sealed to said second periphery to form a first space,
an inlet to said first space, said inlet being positioned at a first end of said filter apparatus,
a hydrophilic filter sealed to an inner surface of said second housing portion to form a second space,
said hydrophilic filter separating said first space from said second space, said inner surface having ridges to define a plurality of flow paths and at least one channel, said flow paths being closed at a distal end of said surface remote from said inlet and being open at an opposing end of said surface adjacent said inlet, said flow paths being connected to said at least one channel at said opposing end, said at least one channel being connected to an outlet positioned at a second end of said filter apparatus opposite said first end thereby to effect fluid flow in said at least one channel in a direction opposite a direction of fluid flow in said flow paths said at least one channel being positioned on substantially the same plane as said flow paths, and said inlet and said outlet being formed integrally on said second housing.

2. The filter apparatus holder of claim 1 wherein said flow paths and said at least one channel are essentially parallel.

3. The filter apparatus of claim 1 having a plurality of channels.

4. The filter apparatus of claim 1 wherein said hydrophilic filter is a cellulose ester.

5. The filter apparatus of claim 1 wherein said first housing portion includes gas vents and a hydrophobic membrane covering said vents.

6. The filter apparatus of claim 5 wherein said hydrophobic membrane is polyvinylidene fluoride.

7. The filter apparatus of claim 5 wherein said hydrophobic membrane is polytetrafluoroethylene.

8. A filter apparatus comprising a first housing portion first periphery, a second housing portion having a second periphery and a core portion having a third periphery on a first surface and a fourth periphery on a second surface, first periphery being sealed to said third periphery and said second periphery being sealed to said fourth periphery thereby to form a first space between said first housing portion and said core and to form a second space between said second housing portion and said core portion, an inlet to said first space and second space, said inlet being positioned at a first end of said filter apparatus, each of said first surface and said second surface having ridges to define a plurality of flow paths and at least one channel, said flow paths being sealed at a distant end of their respective surface remote from said inlet and being open at an opposing end of their respective surface adjacent said inlet, said flow paths being connected to said at least one channel, said at least one channel being connected to an outlet positioned at a second end of said filter apparatus opposite said first end thereby to effect fluid flow in each of said at least one channel in a direction opposite fluid flow in said flow paths, said at least one channel being positioned on substantially the same plane as said flow paths, said first surface being sealed from said first space by a first hydrophilic membrane, said second surface being sealed from said second pace by a second hydrophilic membrane, said inlet and said outlet being formed integrally on said core.

9. The filter apparatus of claim 8 wherein said first housing portion has vent holes sealed with a first hydrophobic membrane and said second housing portion has vent holes sealed with a second hydrophobic membrane.

10. The filter apparatus of claim 8 wherein said flow paths and said at least one channel are essentially parallel.

11. The filter apparatus of claim 8 having a plurality of channels.

12. The filter apparatus of claim 8 wherein said hydrophilic membranes are a cellulose ester.

13. The filter apparatus of claim 9 wherein said hydrophobic membranes are polytetrafluoroethylene.

14. The filter apparatus of claim 9 wherein said hydrophobic membranes are polyvinylidene fluoride.

15. A core portion for use in a filter apparatus in conjunction with a housing portion, said core portion having a first surface having a plurality of ridges to define a plurality of flow paths and at least one channel, said flow paths being sealed at a distant end of said first surface remote from an inlet and being open at an opposing end of said first surface adjacent said inlet, said at least one channel being positioned on substantially the same plane as said flow paths, said flow paths being connected to said at least one channel at said opposing end of said first surface, said at least one channel being in fluid communication with an outlet, a first peripheral surface surrounding said first surface, a first hydrophilic membrane sealed to said first peripheral surface, said inlet being sealed from said outlet by said first hydrophilic membrane, said core portion having a second surface having a plurality of ridges to define a plurality of flow paths and said at least one channel, said flow paths being sealed at a distant end of said second surface remote from said inlet and being open at an opposing end of said second surface adjacent said inlet, said inlet being formed integrally at a first end of said core portion and being in fluid communication with said first surface and said second surface, said outlet being formed integrally at a second end of said core portion and being in fluid communication with said at least one channel, said flow paths being connected to with said at least one channel, said at least one channel being connected to said outlet, a second peripheral surface surrounding said second surface, and said inlet being sealed from said outlet by said second hydrophilic membrane.

16. The core portion of claim 15 wherein said flow paths and said channels are essentially parallel.

17. The core portion of claim 15 having a plurality of channels.

18. A core portion for use in a filter holder in conjunction with a housing portion, said core portion having a first surface having a plurality of ridges to define a plurality of flow paths and at least one channel, said flow paths being sealed at a distant end of said first surface remote from said inlet and being open at an opposing end of said first surface remote from an inlet and being open at an opposing end of said first surface adjacent said inlet, said at least one channel being positioned on substantially the same plane as said flow paths, said inlet being formed integrally at it first end of said core portion and being in fluid communication with said first surface, said outlet being formed integrally at a second end of said core portion and being in fluid communication with said at least one channel, a peripheral surface surrounding said first surface, a hydrophilic membrane sealed to said peripheral surface and said inlet being sealed from said outlet by said hydrophilic membrane.

19. The core portion of claim 18 wherein said flow paths and said at least one channel are essentially parallel.

20. The core portion of claim 18 having a plurality of channels.

* * * * *